US010324043B2

(12) United States Patent
Thompson

(10) Patent No.: US 10,324,043 B2
(45) Date of Patent: *Jun. 18, 2019

(54) METHOD FOR PRE AND POST IMAGE ASSOCIATION IN FIBER OPTIC INSPECTION

(71) Applicant: AFL TELECOMMUNICATIONS LLC, Duncan, SC (US)

(72) Inventor: William Henry Thompson, Westborough, MA (US)

(73) Assignee: AFL Telecommunications LLC, Duncan, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/842,188

(22) Filed: Dec. 14, 2017

(65) Prior Publication Data

US 2018/0106730 A1 Apr. 19, 2018

Related U.S. Application Data

(63) Continuation of application No. 14/124,115, filed as application No. PCT/US2012/043452 on Jun. 21, 2012, now Pat. No. 9,880,105.

(60) Provisional application No. 61/499,440, filed on Jun. 21, 2011.

(51) Int. Cl.
*H04N 9/47* (2006.01)
*H04N 7/18* (2006.01)
*G01N 21/00* (2006.01)
*G01N 21/94* (2006.01)
(Continued)

(52) U.S. Cl.
CPC ............. *G01N 21/94* (2013.01); *G01M 11/31* (2013.01); *G02B 6/385* (2013.01)

(58) Field of Classification Search
CPC ...... G01M 11/081; G01M 11/31; G01N 21/94
See application file for complete search history.

(56) References Cited

U.S. PATENT DOCUMENTS 5,995,212 A * 11/1999 Dar ................... G01N 21/952
356/73.1
6,287,020 B1 9/2001 Osaka
6,765,658 B2 7/2004 Nguyen et al.
(Continued)

OTHER PUBLICATIONS

Fluke Networks, "Optical Fiber Cabling for Data Communication—Test and Troubleshooting Quick-Reference Guide," Fluke Corporation, Everett, Washington, USA, 2009 (24 pages).
(Continued)

*Primary Examiner* — Rebecca A Volentine
(74) *Attorney, Agent, or Firm* — Dority & Manning, P.A.

(57) ABSTRACT

A fiber optic connector inspection display system including: a input unit which receives fiber end-face images; a display mode election unit which allows a user to select at least one of an image capture mode or an image review mode; a capturing unit which captures the fiber end-face images; a storing unit which stores the captured images as a first still image and a second still image; a display unit which displays the received fiber end-face images from the input unit or the stored first and second still images, and a control unit which stores each of the first and second still images with a user defined identification label, and the control unit may further label the each of the first and second still images with a preset image pair mode label if the user selects a preset image pair mode.

17 Claims, 12 Drawing Sheets

(51) Int. Cl.
*G01M 11/00* (2006.01)
*G02B 6/38* (2006.01)

(56) References Cited

U.S. PATENT DOCUMENTS

| | | |
|---|---|---|
| 6,798,515 B1 | 9/2004 | Bachelder |
| 6,989,895 B2 | 1/2006 | Buzzetti |
| 7,003,200 B2 | 2/2006 | Huang |
| 7,061,522 B1 | 6/2006 | Kojima |
| 7,162,073 B1 | 1/2007 | Akgul |
| 7,847,251 B1 | 12/2010 | Praly |
| 8,306,760 B1 | 11/2012 | Koudelka |
| 9,110,251 B2 | 8/2015 | Chen |
| 2002/0109831 A1 | 8/2002 | Van Nguyen |
| 2004/0125366 A1 | 7/2004 | Kiani |
| 2005/0281456 A1 | 12/2005 | Garvey |
| 2008/0240545 A1 | 10/2008 | Endo |
| 2008/0304051 A1 | 12/2008 | Wells |
| 2009/0010601 A1* | 1/2009 | Huang ................ G02B 6/2551 385/97 |
| 2009/0159814 A1 | 6/2009 | Maiya |
| 2010/0141934 A1 | 6/2010 | Narum et al. |
| 2011/0064366 A1 | 3/2011 | Zheng |
| 2011/0085159 A1 | 4/2011 | Levin |
| 2012/0050523 A1 | 3/2012 | Cook |
| 2012/0314084 A1 | 12/2012 | Lammert |
| 2013/0156307 A1 | 6/2013 | Yates |

OTHER PUBLICATIONS

AFL Telecommunications LLC, International Patent Application No. PCT/US2012/043452; International Search Report; Sep. 20, 2012, 1 page.

* cited by examiner front view top view bottom view side view back view

Image Explorer

Image Review

Snapshot

Live Image

METHOD FOR PRE AND POST IMAGE ASSOCIATION IN FIBER OPTIC INSPECTION

CROSS-REFERENCE TO RELATED APPLICATIONS

This application is a Continuation Application of U.S. patent application Ser. No. 14/124,115, filed Dec. 5, 2013, which is a National Stage Application of PCT/US2012/043452, filed on Jun. 21, 2012, which is based upon and claims the benefit of priority from U.S. Provisional Patent Application No. 61/499,440, filed Jun. 21, 2011, the disclosures of all of which are incorporated by reference herein in their entireties.

BACKGROUND

1. Field

Apparatuses and methods consistent with the exemplary embodiments relate to a fiber optic connector inspection display system, and more particularly, a fiber optic connector inspection display system which is capable of associating and linking related images and displaying the same.

2. Related Art

Fiber and connector contamination is a key contributor to network downtime and there is a need to document that fibers and connectors have been properly cleaned during installation and subsequent network activation and maintenance tasks. Clean fiber optic components are a requirement for quality connections between fiber optic equipment. One of the most basic and important procedures for the maintenance of fiber optic systems is to clean the fiber optic equipment.

Any contamination in the fiber connection can cause failure of the component or failure of the whole system. Even microscopic dust particles can cause a variety of problems for optical connections. A particle that partially or completely blocks the core generates strong back reflections, which can cause instability or failure in the laser system. Dust particles trapped between two fiber faces can scratch the glass surfaces. Even if a particle is only situated on the cladding or the edge of the end-face, it can cause an air gap or misalignment between the fiber cores which significantly degrades the optical signal.

Typically, technicians are given very basic tools, such as miniature optical microscopes or crude video microscopes to perform inspections, but these can neither document results nor provide pass/fail analysis. Thus, some fibers may not be inspected at all and those that are at the mercy of the subjective decisions of field technicians.

Further, if the technicians are given a task to inspect and take a snap shot of condition of the equipment at one point in time and come back in the future at a different point in time to repeat the same task, there is no easy way to linking the related snapshots of the equipment to compare the images efficiently.

SUMMARY

One or more exemplary embodiments may overcome the above disadvantages and other disadvantages not described above. However, it is understood that one or more exemplary embodiment are not required to overcome the disadvantages described above, and may not overcome any of the problems described above.

Accordingly, aspects of one or more exemplary embodiments may be achieved by providing a fiber optic connector inspection display system including: a input unit which receives fiber end-face images; a display mode selection unit which allows a user to select as least one of an image capture mode or an image review mode; a capturing unit which captures the fiber end-face images; a storing unit which stores the captured images as a first still image and a second still image; a display unit which displays the received fiber end-face images from the input unit or the stored first and second still images, and a control unit which stores each of the first and second still images with a user defined identification label, and the control unit way further label the each of the first and second still images with a preset image pair mode label if the user selects a preset image pair mode.

The control unit may couple the first still image and the second still image if the first and the second still image has the same user defined identification label and the same preset image pair mode label.

The preset image pair mode may include at least one of before/after, input/output, cleaning, mating and documentation preset.

The fiber optic connector inspection display system way further include a filtering unit which fibers the stored images based on the at least one of the before/after, the input/output, the cleaning, the mating and the documentation preset.

Another aspects of one or more exemplary embodiments may be achieved by providing a method of analyzing fiber optic connector inspection images, the method including: selecting an image capture mode; receiving fiber end-face images; capturing the fiber end-face images as a first still image and a second still image; storing each of the first and second still image with a user defined identification label; storing the first and second still image with a preset image pair mode label if a user selects a preset image pair mode, selecting an image review mode; and displaying the received fiber end-face images from the input unit or she stored first and second still images.

The method may further include coupling the first still image and the second still image if the first and the second still image has the same user defined identification label and the same preset image pair mode label.

The preset image pair mode label may include at least one of before/after, input/output, cleaning, mating and documentation.

The method may further include filtering the stored images based on the at least one of the preset image pair mode of before/after, input/output, cleaning, mating and documentation.

Still another aspects of one or more exemplary embodiments may be achieved by providing A non-transitory computer-readable recording medium storing a computer program causing a fiber optic connector inspection display system to execute a method of analyzing fiber optic connector inspection images, the method including: selecting an image capture mode; receiving fiber end-face images; capturing the fiber end-face images as a first still image and a second still image; storing each of the first and second still image with a user defined identification label; storing the first and second still image with a preset image pair mode label if a user selects a preset image pair mode, selecting art image review mode; and displaying the received fiber end-face images from the input unit or the stored first and second still images.

DETAILED DESCRIPTION

The following detailed description is provided to assist the reader in gaining a comprehensive understanding of the methods, apparatuses and/or systems described herein. Various changes, modifications, and equivalents of the systems, apparatuses and/or methods described herein will suggest themselves to these of ordinary skill in the art. Descriptions of functions and structures are omitted to enhance clarity and conciseness.

Figure 1A:
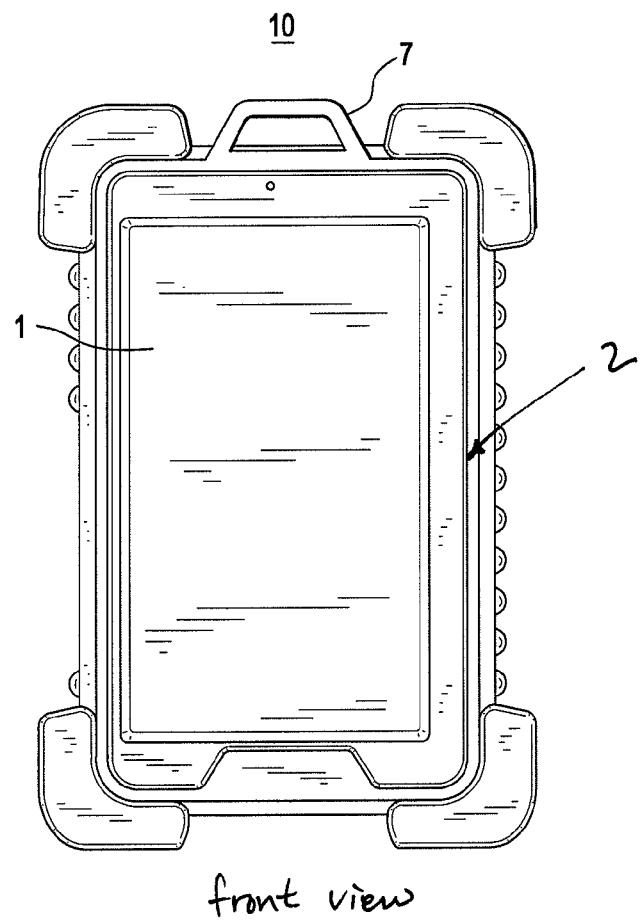
FIGS. 1A-1D show a front, a top, a bottom and a side view of a fiber optic connector inspection display system.
Figure 1B:
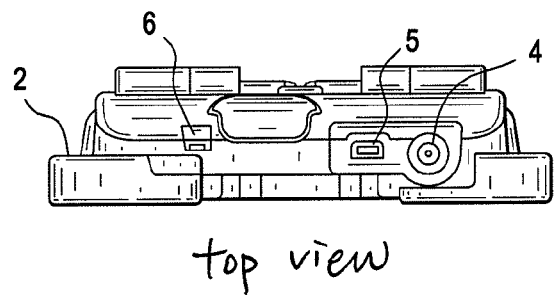
Figure 1C:
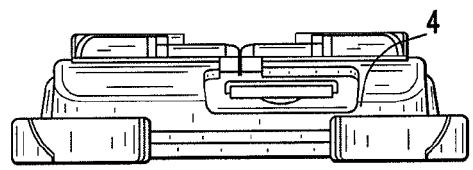
Figure 1D:
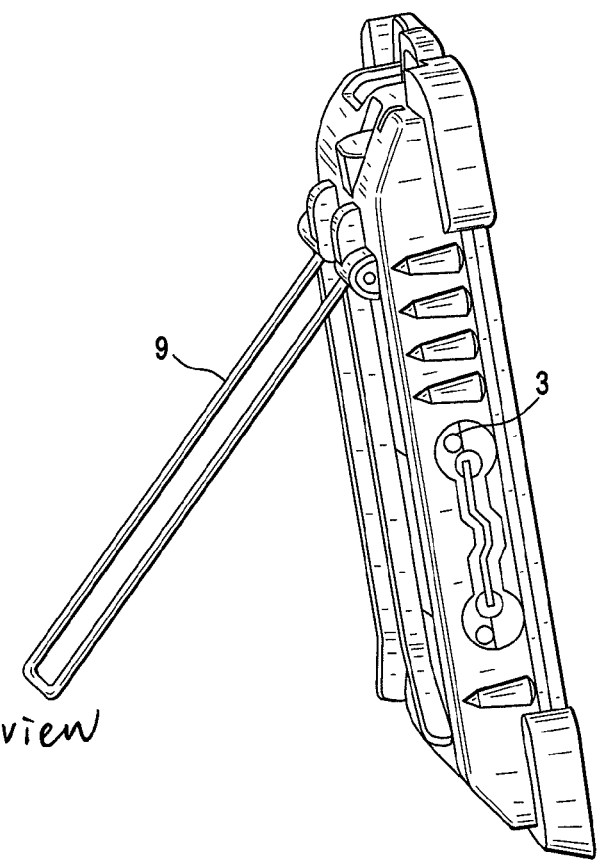
Figure 2A:
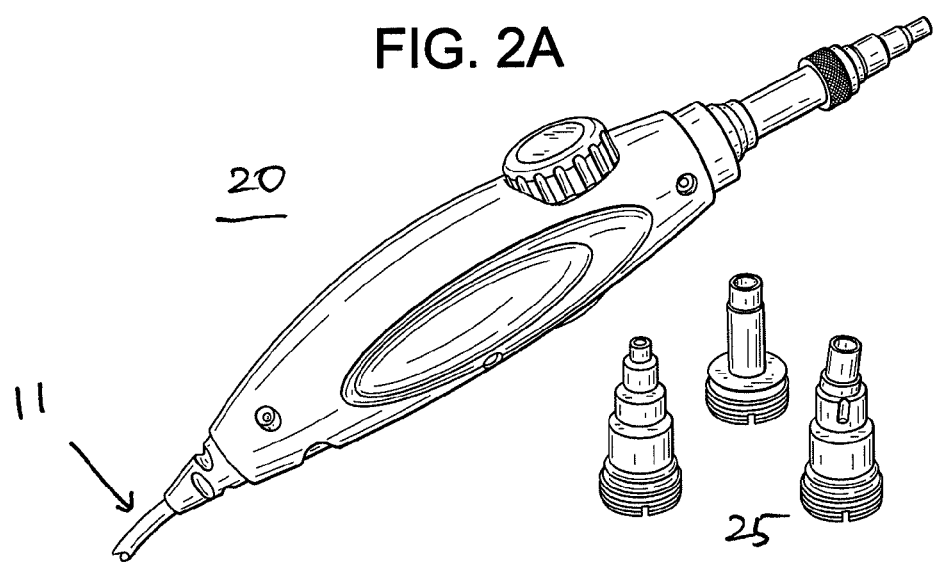
FIG. 2A shows an input fiber scope which can be used with the fiber optic connector inspection display system shown in FIGS. 1A-1D.

FIGS. 1A-1D show a front, a top, a bottom and a side view of a fiber optic connector inspection display system 10. The fiber optic connector inspection system 10 which provides unique new capabilities not supported by any existing video inspection system. The fiber optic connector inspection system is a hand-held display/processor unit (DPU) that can be used with an inspection input fiber scope 20 as shown in FIG. 2A. This solution will give network installation and maintenance personnel installers the ability to inspect and document the condition of fiber connectors and patchcords.

The fiber optic connector inspection system as shown in FIGS. 1A-1D includes a touch screen display 1, a protective boot 2, a power button 3, a power port 4, a universal serial bus (USB) function port 5, a charger indicator 6 and a flash card slot 8.

The touch screen display 1 contains on-screen controls and menus and is used to show live, captured and saved fiber end-face images. The touch screen display 1 also allows a user to select live image setting, image capture modes, general settings and image manager. The boot 8 is a shock-absorbing rubber boot to protect the touch screen display. The power button 3 is used not only for powering up and shutting down the fiber optic connector inspection display system 10 but also for enabling sleep mode to save battery without completely shutting off the fiber optic connector inspection display system 10.

Figure 2B:
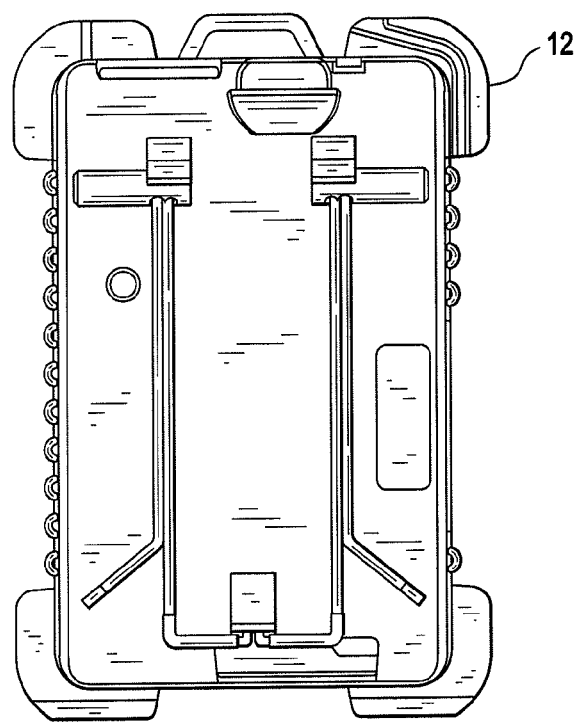
FIG. 2B shows a rear view of the fiber optic connector inspection display system shown in FIGS. 1A-1D with a cable connection to attach the input fiber scope shown in FIG. 2A.

The power port 4 is an interface for the AC power adaptor and charger and the universal serial bus (USB) function port 5 allows connection to the inspection input fiber scope 20 as shown in FIG. 2 through a converter cable 11 shown in FIG. 2A. The charger indicator 6 indicates whether the AC adaptor (not shown) is connected to the fiber optic connector inspection display system 10 and different colors indicates whether a battery (not shown) is charging (red) or is fully charged (green). The flash card slot 8 is used for retain a flash card which can be used for storing and transferring fiber end-face images to another system such as a personal computer or a laptop. In addition to the flash card mechanism so described, fiber end-face images may also be transferred, via a USB memory device connected to the USB function port 5.

The fiber optic connector inspection display system 10 may also include a loop 7 which can be used as a hanger or a bail 9, which can be used as a tilt stand or another hanger. The fiber optic connector inspection display system 10 may also include a cable retainer 12 which is designed to provide strain relief for the converter cable 11 shown in FIG. 2A.

FIG. 2A shows an input fiber scope 20 which can be used with the fiber optic connector inspection display system 10 shown in FIGS. 1A-1D. The input fiber scope 20 shown in FIG. 2A is one of many fiber scope equipment available in the market. FIG. 2A also shows different types of probe head 25 which can be used for different fiber optic equipments.

Figure 3:
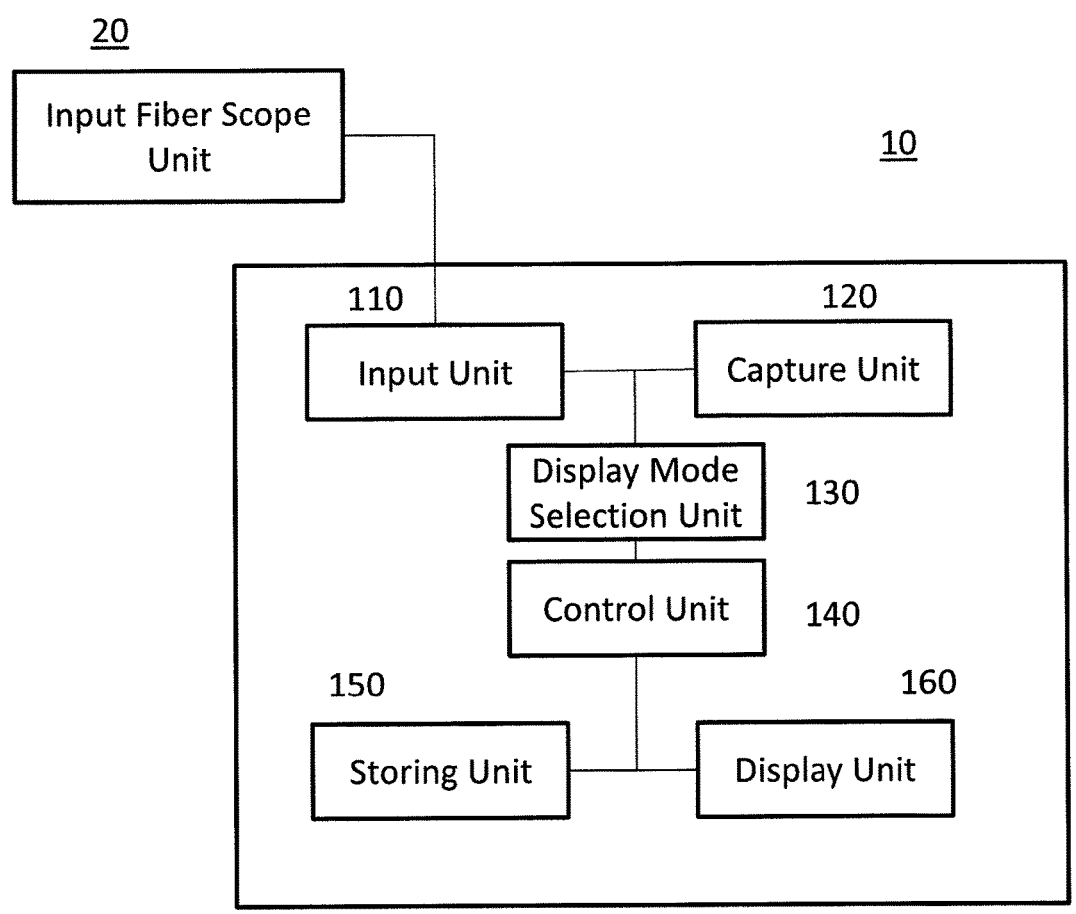
FIG. 3 shows a block diagram of a fiber optic connector inspection display system according to an exemplary embodiment.

FIG. 3 shows a block diagram of a fiber optic connector inspection display system according to an exemplary embodiment. Referring to FIG. 3, the fiber optic connector inspection display system 10 according to the present embodiment includes an input unit 110 receiving fiber end-face images from a input fiber scope unit 20, a capture unit 120 capturing the fiber end-face images through the input fiber scope unit, a display mode selection unit 130, a control unit 140, a storing unit 150 which stores the captured images and a display unit 160 which can display various modes selected from the mode selection unit and display images accordingly.

Figure 4:
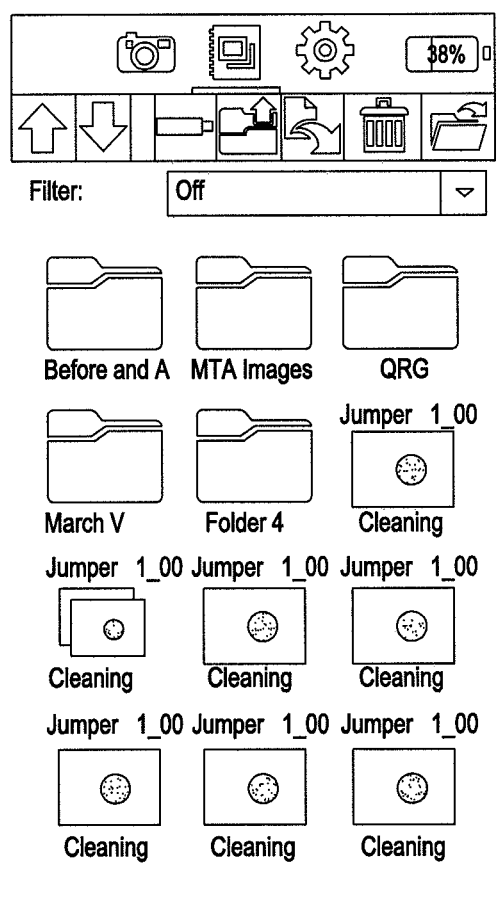
FIG. 4 shows a display unit displaying images that are organized and stored in a storage unit of a fiber optic connector inspection display system.
Figure 5C:
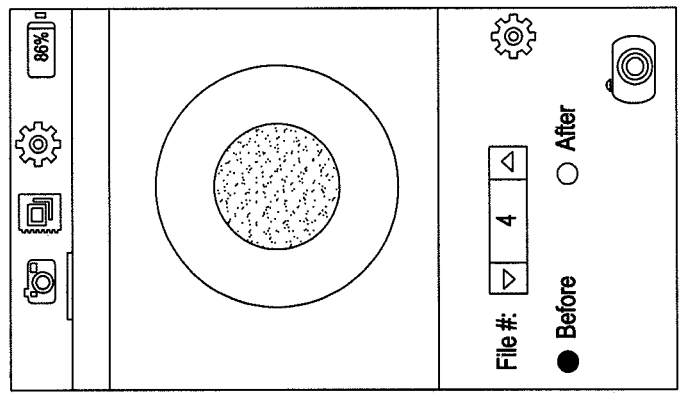
FIGS. 5A-5C show a display unit which can display a live image mode, a capture mode and a image review mode.
Figure 5B:
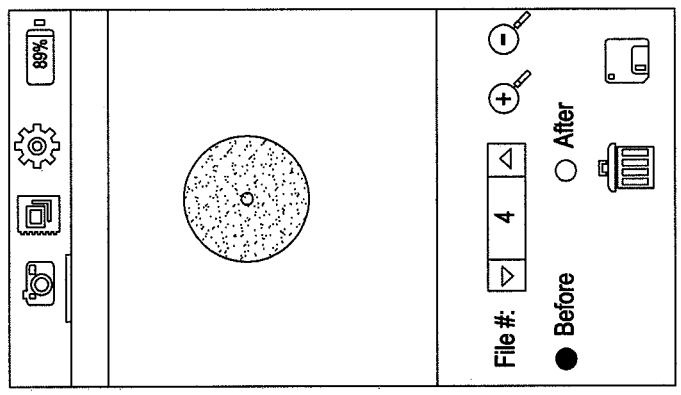
Figure 5A:
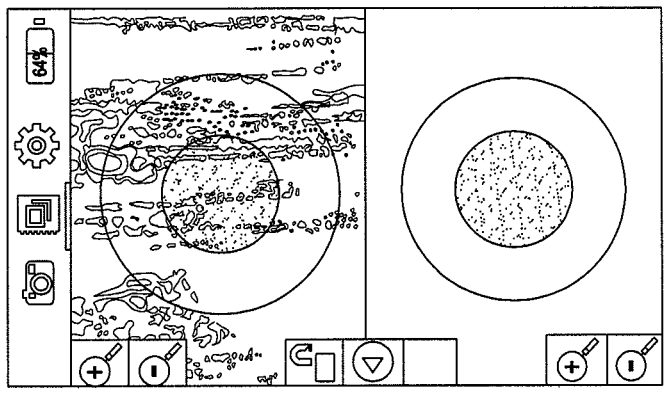
Figure 6:
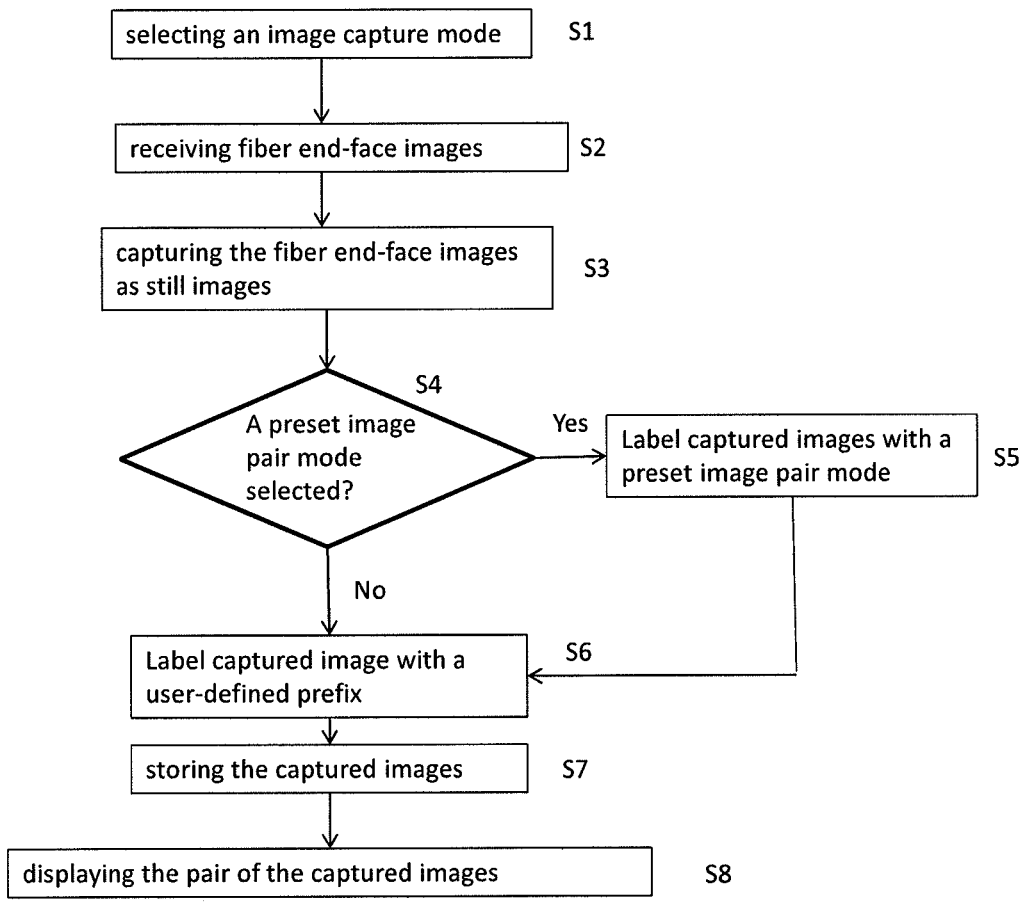
FIG. 6 shows a flowchart illustrating the method of linking a pair of related images using a fiber optic connector inspection display system.

The display mode selection unit 130 allows a user to select from at least one of live image mode, snapshot mode, image explore mode and image review mode as shown in FIG. 4 and FIGS. 5A-5C. In the live image mode as shown in FIG. 5A, the user can view a live view of the fiber optic equipment of interest. This mode allows the user to zoom or pan to focus on the area of interest. Once the user determines that documentation is required on the fiber optic equipment of interest, the user may switch from the live image mode to the snapshot mode. In snapshot mode as shown in FIG. 5B, the user can capture an image of interest and the fiber optic connector inspection display system 10 provides preview of the captured image. Once the user saves the captured image, the user can find the stored images via image explore mode as shown in FIG. 4. In the image explore mode, the user has options to save images into specific folders and delete files. Finally, as shown in FIG. 5C, the user can view the stored images selected from the image explorer view in FIG. 4.

Hereinafter, the control unit 140 will be described in detail. The control unit controls the a input fiber scope unit 20, a capture unit 120, a display mode selection unit 130, a storing unit 150 and a display unit 160 based on the user instructions through a touch screen of the fiber optic connector inspection display system 10. In addition to the basic function of controlling other units of the fiber optic connector inspection display system 10 as described above, the control unit 140 provides a user an image pair mode function.

By enabling the image pair mode allows the user to select a preset pair mode prior to fibers inspection, to inspect fiber end-faces and to save captured images with the selected pairing preset label for simplified identification, recall and review. In order to use advantages of the image pair mode, the user first selects a preset image pairing mode prior to fibers inspection. Table 1 below shows the available image presets. However, the presets of exemplary embodiment shown in Table 1 are not limited thereto and the one of ordinary skill in the art may create other image pair presets

TABLE 1

| Image Pair Preset | Description |
| --- | --- |
| Before/after | This is a general preset for any before/after fiber inspection comparisons |
| Input/output | This is a general preset for any input/output fiber inspection comparison |
| Cleaning | This preset is used for inspection fiber end-faces before and after cleaning |
| Mating | This preset is used for inspection of mating connector and bulkhead |
| Documentation | This preset is used for as-built/as-found fiber installation and maintenance |

After the image pair mode is enabled, captured images are stored with the selected pairing mode label as shown in Table 1 (Before/After, Input/Output, Cleaning, Mating and Documentation) for image pair identification. Finally, to simplify images recall and review, stored images may be optionally filtered by the user-selected image pair mode in the image explorer display mode.

Hereinafter, an illustration is provided as to how a technician takes advantage of the image pairing mode feature to document a service call with reference to FIGS. 7A-7G. Contaminated or damaged fiber optic connectors have been identified as the root cause of many network outages. Upon receipt of a customer complaint, the technician is dispatched to customer premise. If the contamination or the fiber end-face damage is encountered, the technician should unequivocally document the contamination of the damage.

Figure 7C:
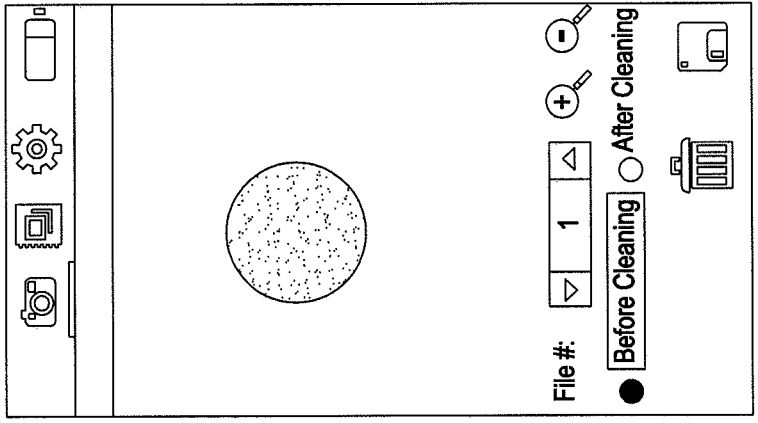
FIGS. 7A-7G show an example of how a technician can, in step by step, document a before and after cleaning of fiber optic equipment.
Figure 7B:
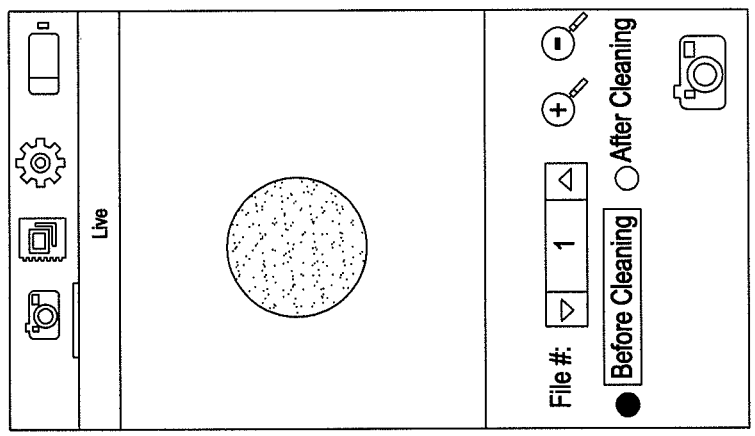
Figure 7A:
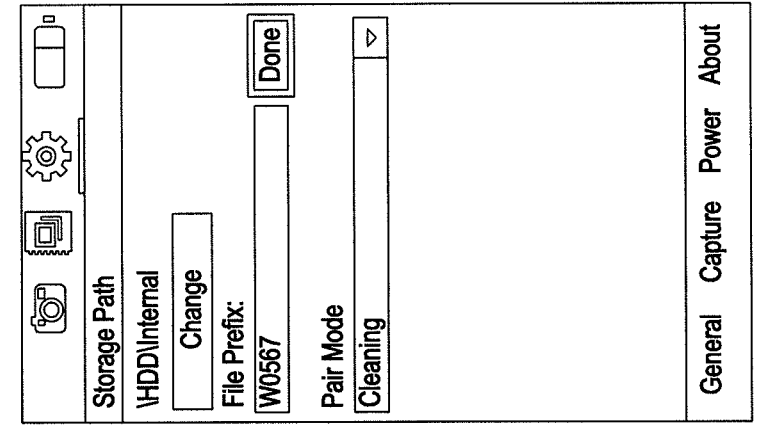
Figure 7F:
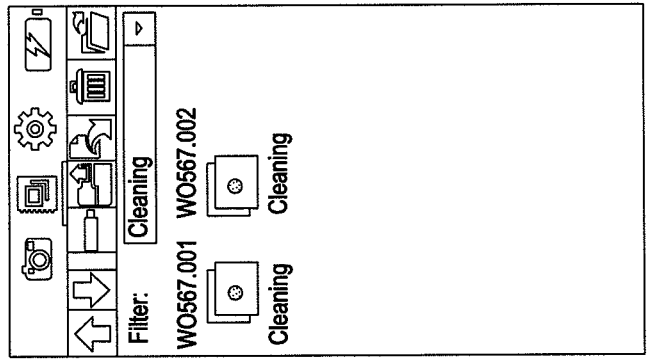
Figure 7E:
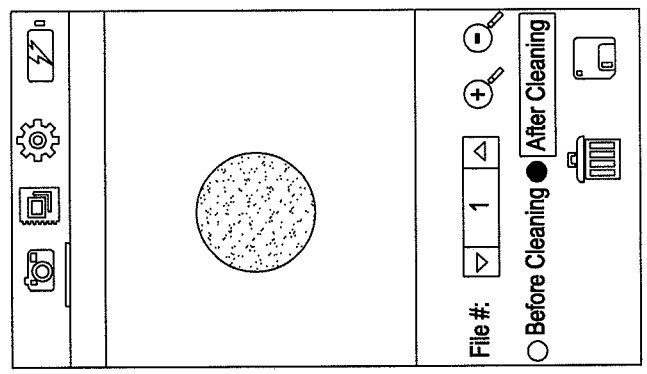
Figure 7D:
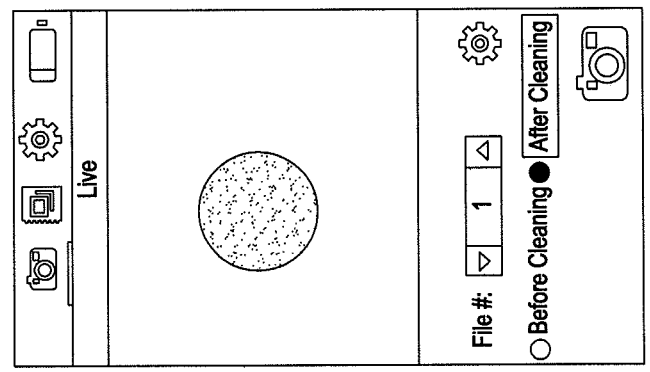
Figure 7G:
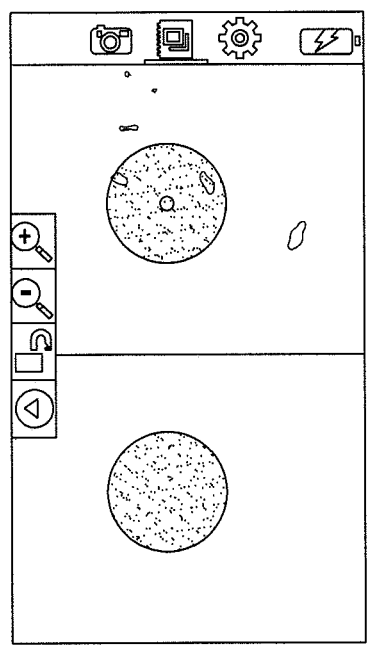

As shown in FIG. 7A, using the Settings tab 201, the technician chooses "Cleaning" pair mode, and insert the file identification as a file prefix 202. For example, technician may use work order number (# WO567) as the file prefix. After disassembling a suspect fiber optic connector, using image video probe, the user can view a "Before Cleaning" image of one of the mating portions of the connector as shown in FIG. 7B in a live image view mode 203. Referring to FIG. 7C, using Snapshot capability 204, the technician captures the image and store the "Before Cleaning" image in the storage unit 150. Once the technician cleans the suspect fiber end-face and then the technician views the end-face image after the cleaning. As shown in FIG. 7D, the technician selects "After Cleaning" and sets "File #" to 1. If the technician is satisfied with cleanliness of the fiber end-face, use Snapshot capability to capture the image and store the "After Cleaning" image in the storage unit 150 as shown in FIG. 7E. Repeat this process with the other mating portion of fiber connector using File #2. As a result, two paired images are stored in the storage unit 150 as shown in FIG. 7F. In FIG. 7F, by selecting "Cleaning" in the filter setting 205, only pairs with "Cleaning," as a pair mode are displayed. As shown in FIG. 7G, opening the "WO567_002" from FIG. 7F allows the technicians to see a comparison of the before (topmost) and after (bottommost) images of the file. In this case the view sees that all of the dirt and contamination present in the before view has been removed.

Hereinafter, another illustration is provided as to how a technician takes advantage of the image pairing mode feature to associate related images with reference to FIGS. 8A-8D. In the current illustration, a technician dispatched to install a fiber option equipment at an arbitrary customer location. As an illustration purpose only, "2 West Main Street" will be used as the address of the easterner location.

Figure 8A:
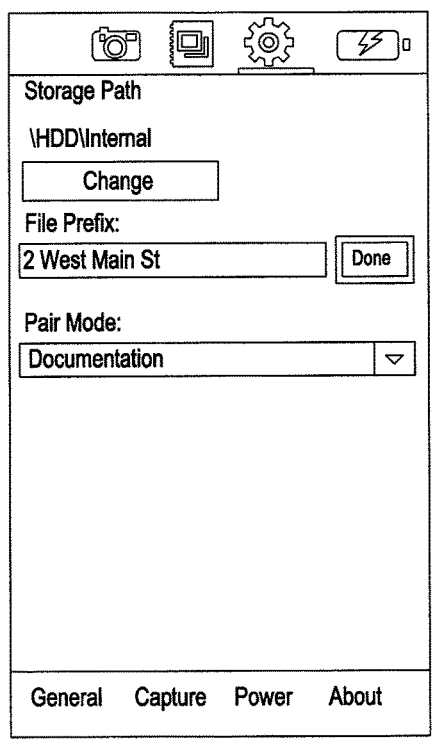
FIGS. 8A-8D show another example of how a technician can, in step by step, document a deterioration of a fiber optic equipment over time.
Figure 8B:
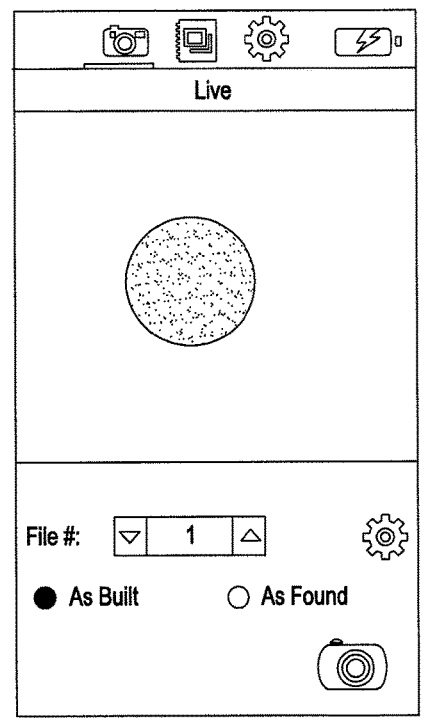
Figure 8C:
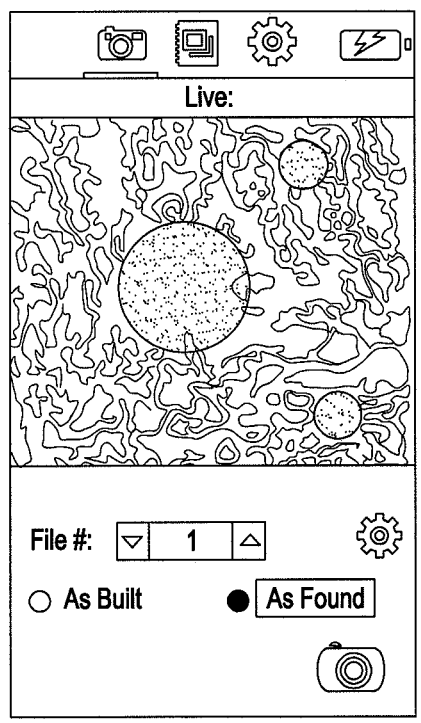
Figure 8D:
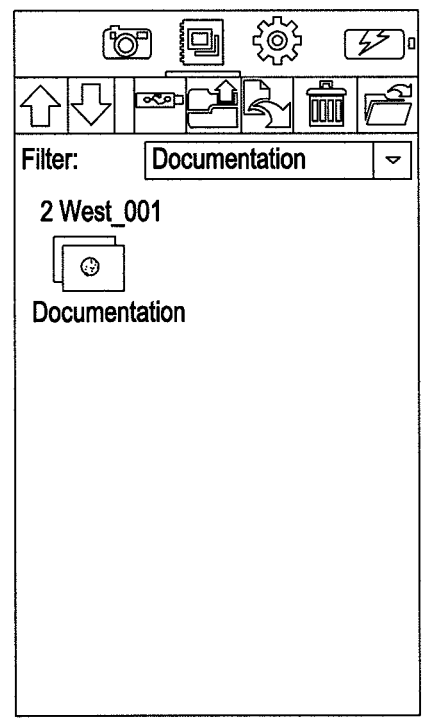

Similar to the illustration above, using the Settings tab 301, the technician chooses "Documentation" pairing mode (As Built/As Found) as shown in FIG. 8A. The technician sets "2 West Main Street" as the File Prefix 302 to easily identify the images to be taken. The technician installs the fiber equipment and documents fiber end-face image cleanliness by selecting "As Built" and File number "1" as shown in FIG. 8B. One year later, in this illustration, the technician receives a customer complaint about the service at "2 West Main Street." The technician creates a pairing of the "As found" with the original "As Built" by simply selecting the documentation mode, using the 2 West Main Street prefix and selecting the "As Found" button. The technician views fiber end-face and finds the equipment contaminated as shown in FIG. 8C. Realizing that he must document his findings he chooses "As Found" and selects file #001. This process results in the creating of the image pair for 2 West Main St. The technician views the pair in the image browser as shown in FIG. 8D. Viewing the image pair simultaneously provides unequivocal proof that the "As Built" condition of the fiber end-face was somehow degraded through misuse, tampering, environmental conditions or other mechanisms.

So far, examples of coupling images based on "Before Cleaning" with "After Cleaning" and "As Built" with "As Found." However, the examples shown are not limited thereto and any other criteria can be used to couple the images and view the images simultaneously.

Hereinafter, a method of analyzing fiber optic connector inspection images according to an embodiment will be described with reference to FIG. 8.

First, a user selects an image capture mode (S1) and views fiber end-face images (S2). Then the user captures the fiber end-face images as still images (S3). If a preset image pair mode is selected (S4), label the captured image with a preset image pair mode and a user-defined prefix (S5). However, if the preset image pair mode is not selected (S4), label the captured image with only the user-defined prefix (S6) and store the captured image in the storage unit 150 (S7).

Then, the fiber optic connector inspection display system 10 displays the captured image (S8). Here, if the user selects the captured images with the preset image pair mode, the display system 10 can display the pair of captured images simultaneously as shown in FIGS. 5C and 7G.

Although a few exemplary embodiments have been shown and described, it will be appreciated by those skilled in the art that changes may be made in these exemplary embodiments without departing from the principles and spirit of the invention, the scope of which is defined in the appended claims and their equivalents. The exemplary embodiments should be considered in a descriptive sense only and not for purposes of limitation.

What is claimed is:

1. A fiber optic connector inspection display system comprising:
   an input unit which receives fiber end-face images;
   a capturing unit which captures the fiber end-face images;
   a storing unit which stores the captured images as a first still image and a second still image, wherein the second still image includes the same fiber optic equipment of interest as the first still image and is taken at a different time from the first still image; and a control unit which stores each of the first and second still images, wherein the control unit further labels each of the first and second still images with a preset image pair mode label if a preset image pair mode is selected prior to inspection, and wherein the preset image pair mode is for inspection comparisons of the same fiber optic equipment of interest.

2. The fiber optic connector inspection display system of claim 1, wherein the first still image is taken before an event, and wherein the second still image is taken after an event.

3. The fiber optic connector inspection display system of claim 1, further comprising a display unit which displays the received fiber end-face images.

4. The fiber optic connector inspection display system of claim 1, further comprising a display mode selection unit which allows selection of least one of an image capture mode or an image review mode.

5. The fiber optic connector inspection display system of claim 1, wherein the control unit stores each of the first and second still images with a user defined identification label.

6. The fiber optic connector inspection display system of claim 5, wherein the control unit couples the first still image and the second still image if the first and the second still image have the same user defined identification label and the same preset image pair mode label.

7. The fiber optic connector inspection display system of claim 1, wherein the preset image pair mode comprises at least one of before/after, input/output, cleaning, mating or documentation preset.

8. The fiber optic connector inspection display system of claim 1, further comprising a filtering unit which filters the stored images based on the at least one of the before/after, the input/output, the cleaning, the mating or the documentation preset.

9. A method of analyzing fiber optic connector inspection images, the method comprising:

capturing fiber end-face images as a first still image and a second still image, wherein the second still image includes the same fiber optic equipment of interest as the first still image and is taken at a different time from the first still image; and storing each of the first and second still image, wherein if a preset image pair mode is selected prior to inspection, the first and second still images are stored with a preset image pair mode label, and wherein the preset image pair mode is for inspection comparisons of the same fiber optic equipment of interest.

10. The method of claim 9, wherein the first still image is taken before an event, and wherein the second still image is taken after an event.

11. The method of claim 9, wherein the preset image pair mode is for inspection comparisons of the same fiber optic equipment of interest before and after an event.

12. The method of claim 9, further comprising selecting an image capture mode.

13. The method of claim 9, further comprising selecting an image review mode; and displaying the stored fiber end-face images.

14. The method of claim 9, wherein each of the first and second still images is stored with a user defined identification label.

15. The method of claim 14, further comprising coupling the first still image and the second still image if the first and the second still image have the same user defined identification label and the same preset image pair mode label.

16. The method of claim 9, wherein the preset image pair mode label comprises at least one of before/after, input/output, cleaning, mating or documentation.

17. The method of claim 9, further comprising filtering the stored images based on the at least one of the preset image pair mode of before/after, input/output, cleaning, mating or documentation.

* * * * *